US00PP13232P2

(12) United States Plant Patent
Hofmann

(10) Patent No.: US PP13,232 P2
(45) Date of Patent: Nov. 12, 2002

(54) NEW GUINEA IMPATIENS PLANT NAMED 'FISNICS DARK SALMON'

(76) Inventor: Birgit Hofmann, Gassenweg 29, 56170 Bendorf (DE)

( * ) Notice: Subject to any disclaimer, the term of this patent is extended or adjusted under 35 U.S.C. 154(b) by 22 days.

(21) Appl. No.: 09/921,490

(22) Filed: Aug. 6, 2001

(51) Int. Cl.[7] ..... A01H 5/00
(52) U.S. Cl. ..... Plt./318

(58) Field of Search ..... Plt./318

*Primary Examiner*—Kent L. Bell
(74) *Attorney, Agent, or Firm*—C. A. Whealy

(57) ABSTRACT

A new and distinct cultivar of New Guinea Impatiens plant named 'Fisnics Dark Salmon', characterized by its compact, rounded and uniformly mounded plant habit; freely branching and freely flowering habit; large rounded dark salmon orange-colored flowers that are positioned above and beyond the foliage; and dark green-colored leaves.

1 Drawing Sheet

BOTANICAL CLASSIFICATION/CULTIVAR DESIGNATION

*Impatiens hawkeri* cultivar 'Fisnics Dark Salmon'.

BACKGROUND OF THE INVENTION

The present Invention relates to a new and distinct cultivar of New Guinea Impatiens plant, botanically known as *Impatiens hawkeri*, and hereinafter referred to by the name 'Fisnics Dark Salmon'.

The new Impatiens is a product of a planned breeding program conducted by the Inventor in Hillscheid, Germany. The objective of the breeding program is to develop new Impatiens cultivars that flower relatively early and have large rounded flowers with attractive flower color.

The new Impatiens originated from a cross made by the Inventor in May, 1997 of the *Impatiens hawkeri* cultivar 'Riviera Hot Rose', not patented, as the female, or seed parent, with the *Impatiens hawkeri* cultivar 'Grenada', disclosed in U.S. Plant Pat. No. 9,343, as the male, or pollen parent. The cultivar 'Fisnics Dark Salmon' was discovered and selected by the Inventor as a flowering plant within the progeny of the stated cross in a controlled environment in Moncarapacho, Portugal in March, 1998.

Asexual reproduction of the new cultivar by terminal cuttings taken in Moncarapacho, Portugal, since March, 1998, has shown that the unique features of this new Impatiens are stable and reproduced true to type in successive generations.

SUMMARY OF THE INVENTION

The following traits have been repeatedly observed and are determined to be the unique characteristics of 'Fisnics Dark Salmon'. These characteristics in combination distinguish 'Fisnics Dark Salmon' as a new and distinct Impatiens cultivar:

1. Compact, rounded and uniformly mounded plant habit.

2. Freely branching and freely flowering habit.

3. Large rounded dark salmon orange-colored flowers that are positioned above and beyond the foliage.

4. Dark green-colored leaves.

Plants of the new Impatiens can be compared to plants of the female parent, the cultivar 'Riviera Hot Rose'. In side-by-side comparisons conducted by the Inventor in Hillscheid, Germany, plants of the new Impatiens differed from plants of the cultivar 'Riviera Hot Rose' in the following characteristics:

1. Plants of the new Impatiens have darker green foliage than plants of the cultivar 'Riviera Hot Rose'.

2. Flower color of plants of the new Impatiens is dark salmon orange whereas flower color of plants of the cultivar 'Riviera Hot Rose' is salmon rose to carmine.

Plants of the new Impatiens can be compared to plants of the male parent, the cultivar 'Grenada'. In side-by-side comparisons conducted by the Inventor in Hillscheid, Germany, plants of the new Impatiens differed from plants of the cultivar 'Grenada' in the following characteristics:

1. Plants of the new Impatiens have larger flowers than plants of the cultivar 'Grenada'.

2. Flower color of plants of the new Impatiens is dark salmon orange whereas flower color of plants of the cultivar 'Grenada' is salmon pink.

3. Stem color of plants of the new Impatiens is darker red purple than stem color of plants of the cultivar 'Grenada'.

Plants of the new Impatiens are similar to plants of the cultivar 'Danhardpsal', not patented, in flower color. However, in side-by-side comparisons conducted by the Inventor in Hillscheid, Germany, plants of the new Impatiens differed from plants of the cultivar 'Danhardpsal' in the following characteristics:

1. Plants of the new Impatiens are more compact, are more freely branching and have shorter internodes than plants of the cultivar 'Danhardpsal'.

2. Plants of the new Impatiens have darker green foliage than plants of the cultivar 'Danhardpsal'.

3. Flower color of plants of the new Impatiens is more intense and more uniform than flower color of plants of the cultivar 'Danhardpsal'.

4. Stem color of plants of the new Impatiens is dark red purple whereas stem color of plants of the cultivar 'Danhardpsal' is light green.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens.

The photograph comprises a side perspective view of a typical flowering plant of 'Fisnics Dark Salmon' grown in a 12-cm container about 10 to 11 weeks after planting a young rooted plant.

DETAILED BOTANICAL DESCRIPTION

The cultivar 'Fisnics Dark Salmon' has not been observed under all possible environmental conditions. The phenotype may vary somewhat with variations in environment such as temperature, light intensity, daylength, water status and/or fertility level, without, however, any variance in genotype.

The following observations and measurements describe plants grown in Hillscheid, Germany, under commercial practice in a glass-covered greenhouse. Rooted young plants were planted in 12-cm containers in late February and the following observations and measurements were taken about 10 to 11 weeks later. During the production of the plants, day temperatures ranged from 18 to 24° C. and night temperatures were about 18° C. In the following description, color references are made to The Royal Horticultural Society Colour Chart except where general terms of ordinary dictionary significance are used.

Commercial classification: New Guinea Impatiens cultivar 'Fisnics Dark Salmon'.

Parentage:

*Female parent.*—*Impatiens hawkeri* cultivar 'Rivera Hot Rose', not patented.

*Male parent.*—*Impatiens hawkeri* cultivar 'Grenada', disclosed in U.S. Plant Pat. No. 9,343.

Propagation:

*Type cutting.*—Terminal tip cuttings.

*Time to initiate roots.*—Summer: About 8 to 9 days at 24° C. Winter: About 10 days at 21° C.

*Time to produce a rooted cutting.*—Summer: About 15 days at 24° C. Winter: About 18 days at 21° C.

*Root description.*—Numerous, fibrous, and freely branching; 158D to 179D in color.

Plant description:

*General appearance.*—Compact, low, rounded and uniformly mounded plant growth habit; freely branching and flowering habit.

*Crop time.*—From a rooted cutting, about 10 weeks are required to produce finished flowering plants in 12-cm containers.

*Plant height.*—About 11.5 cm.

*Plant diameter or spread.*—About 32.7 cm.

*Lateral branches.*—Quantity: About 10 to 13 per plant. Length: About 9.75 cm. Diameter: About 6.5 mm. Internode length: About 3 cm. Color: 185A.

*Foliage description.*—Arrangement: Primarily in whorls. Length: About 11 cm. Width: About 4.1 cm. Shape: Elliptic. Apex: Acuminate. Base: Acute. Margin: Serrulate with ciliation. Texture: Smooth, glabrous. Color: Young foliage, upper surface: 137A. Young foliage, lower surface: 185B to 185C. Mature foliage, upper surface: 139A. Mature foliage, lower surface: 185B to 185C. Venation, upper surface: 53A. Venation, lower surface: 53B. Petiole: Length: About 2.75 cm. Diameter: About 3 mm. Color: 53A to 53B.

Flower description:

*Flower type and flowering habit.*—Single and large rounded dark salmon orange-colored flowers. Freely and continuously flowering; usually about 8 to 11 flowers and flower buds per lateral branch. Flowers positioned above and beyond the foliage and typically face upward or outward. Petals self-cleaning; gynoecium persistent. Flowers not fragrant.

*Flower longevity.*—Flowers last about 7 to 10 days on the plant.

*Flowering season.*—Year-round under greenhouse conditions; in the garden, flowering from spring until fall. Plants begin flowering about 9 weeks after planting.

*Flower buds.*—Length: About 2.45 cm. Diameter: About 1.5 cm. Shape: Ovoid. Color: 43A to 43B.

*Flower length.*—About 7.3 cm.

*Flower width.*—About 7.1 cm.

*Flower depth.*—About 1.5 cm.

*Petals.*—Quantity: Five per flower, imbricate. Length: Banner petal: About 3.2 cm. Lateral and base petals: About 3.6 cm. Width: Banner petal: About 4.4 cm. Lateral and base petals: About 5.75 cm. Shape: Roughly cordate. Apex: Emarginate, lobed. Base: Attenuate. Margin: Entire, slightly undulate. Aspect: Mostly flat. Texture: Smooth; satiny. Color: When opening, upper surface: 40A. When opening, lower surface: 43B to 43C. Fully opened, upper surface: 40A to 40B; color fades to 41B with subsequent development; eye zone, between 66B and 66C. Fully opened, lower surface: 43B to 43C.

*Spur.*—Quantity: One per flower. Length: About 5.3 cm. Diameter: At apex: About 0.5 mm. At flower: About 2.2 mm. Aspect: Curved downward. Color: Towards apex, 53B; towards base, 53D.

*Peduncles.*—Length: About 5.6 cm. Diameter: About 2 mm. Strength: Strong, flexible. Color: 154A.

*Reproductive organs.*—Androecium: Stamen number: Five fused at anthers, hooded; filaments free. Anther length: About 7 mm. Anther shape: Obovate. Anther color: 43A. Pollen amount: Moderate. Pollen color: 8D. Gynoecium: Pistil quantity: One per flower. Pistil length: About 4.5 mm. Stigma color: 68A. Ovary: Five-celled. Ovary color: Dark green to olive brown.

*Seeds.*—Seed development has not been observed.

Disease/pest resistance: Plants of the new Impatiens have not been observed to be resistant to pathogens and pests common to Impatiens.

It is claimed:

1. A new and distinct cultivar of New Guinea Impatiens plant named 'Fisnics Dark Salmon', as illustrated and described.

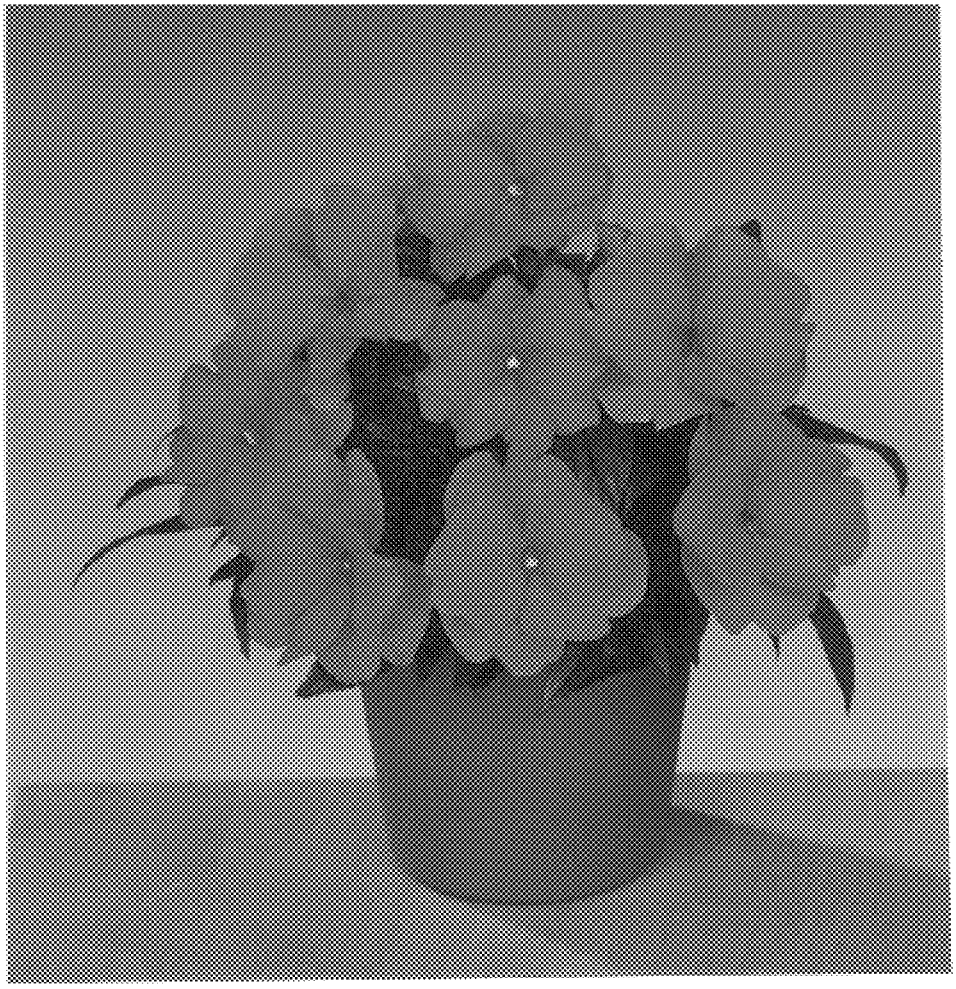

* * * * *